(12) United States Patent
Overweg (10) Patent No.: US 9,498,648 B2
(45) Date of Patent: Nov. 22, 2016

(54) 3D IMAGING METHOD FOR ACCURATE IN-PLANE TRACKING OF LESION TO BE TREATED USING MRGRT

(71) Applicant: KONINKLIJKE PHILIPS N.V., Eindhoven (NL)

(72) Inventor: Johannes Adrianus Overweg, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 31 days.

(21) Appl. No.: 14/417,161

(22) PCT Filed: Jul. 26, 2013

(86) PCT No.: PCT/IB2013/056136
§ 371 (c)(1),
(2) Date: Jan. 25, 2015

(87) PCT Pub. No.: WO2014/016808
PCT Pub. Date: Jan. 30, 2014

(65) Prior Publication Data
US 2015/0209600 A1 Jul. 30, 2015

Related U.S. Application Data

(60) Provisional application No. 61/676,355, filed on Jul. 27, 2012.

(51) Int. Cl.
*G06K 9/00* (2006.01)
*A61N 5/10* (2006.01)
*G01R 33/48* (2006.01)
*A61B 5/055* (2006.01)

(52) U.S. Cl.
CPC ............ *A61N 5/1067* (2013.01); *A61B 5/055* (2013.01); *A61N 5/1049* (2013.01); *G01R 33/4808* (2013.01); *A61N 2005/1055* (2013.01); *A61N 2005/1091* (2013.01)

(58) Field of Classification Search
None
See application file for complete search history.

(56) References Cited

U.S. PATENT DOCUMENTS

| | | | |
|---|---|---|---|
| 6,445,182 B1 * | 9/2002 | Dean | G01R 33/4822 324/307 |
| 2011/0087090 A1 * | 4/2011 | Boernert | A61B 5/055 600/411 |
| 2011/0109314 A1 | 5/2011 | Riederer | |
| 2012/0184841 A1 * | 7/2012 | Nielsen | A61N 5/1031 600/411 |

FOREIGN PATENT DOCUMENTS

| | | |
|---|---|---|
| WO | 2011042820 A1 | 4/2011 |
| WO | 2011127947 A1 | 10/2011 |

OTHER PUBLICATIONS

Chang, Hsuan et al "A Technique for Accurate Magnetic Resonance Imaging in the Presence of Field Inhomogeneities", IEEE Transactions on Medical Imaging, vol. 11, No. 3, Sep. 1992, pp. 319-329.

* cited by examiner

*Primary Examiner* — Hadi Akhavannik (57) ABSTRACT

When monitoring a position of organ(s) at risk (OAR) near a target volume to be irradiated, a LINAC radiation beam source position is identified around a target volume, and a plane perpendicular to a radiation beam is identified. A first phase encoding direction within the plane is assigned, and a second phase encoding direction perpendicular to the first phase encoding direction is assigned. A read-out direction parallel to the radiation beam is assigned, and an MR image of the target volume and any OAR(s) is generated. The position of the target volume relative to the radiation beam is determined and a collimator between the LINAC source and the volume of interest and target volume is controlled to maintain the radiation beam on the target volume and away from any OAR(s) based on the determined position of the target volume.

17 Claims, 5 Drawing Sheets

3D IMAGING METHOD FOR ACCURATE IN-PLANE TRACKING OF LESION TO BE TREATED USING MRGRT

CROSS-REFERENCE TO PRIOR APPLICATIONS

This application is the U.S. National Phase application under 35 U.S.C. §371 of International Application No. PCT/IB2013/056136, filed on Jul. 26, 2013, which claims the benefit of U.S. Provisional Patent Application No. 61/676,355, filed on Jul. 27, 2012. These applications are hereby incorporated by reference herein.

The present application finds particular application in magnetic resonance image guided radiation therapy (MR-gRT) systems. However, it will be appreciated that the described technique may also find application in other multi-modal imaging therapy treatment systems, other medical scenarios, or other clinical techniques.

Linear accelerators (LINAC) are often used in radiation therapy to treat benign and malignant tumors. A LINAC operates by accelerating electrons using a tuned-cavity waveguide to create a standing wave using radio frequency (RF) power. The waveguides may be mounted in the radiation beam direction or at an angle to the radiation beam direction, in which case a bending magnet is employed to deflect the beam towards a target object or patient. Conventional medical grade LINACs use electron beams between 4 and 25 MeV to provide an X-ray output with a plurality of electron energy levels, including an electron energy level that occurs when the electrons are directed at a high-density target (e.g., Tungsten).

When targeting a radiation beam on moving organs, with concurrent real-time MR imaging of the treatment volume, conventional magnetic resonance MR imaging is undesirably sensitive to main field inhomogeneity. Real time high resolution imaging is slow and patient-susceptibility induced distortion occurs in the readout direction.

The present application relates to new and improved systems and methods that facilitate improving efficiency of MR imaging in a combined MR-LINAC system, which overcome the above-referenced problems and others.

In accordance with one aspect, a system that facilitates monitoring a position of a target volume that is being irradiated, includes a magnetic resonance (MR) scanner, a (linear accelerator) LINAC device, and a processor configured to execute computer-executable instructions stored in a memory, the instructions comprising identifying a position of a linear accelerator (LINAC) radiation beam source around a target volume, and identifying an imaging volume of interest defined at one face by a plane perpendicular to a radiation beam emitted by the LINAC source, the volume of interest comprising the target volume and any organ(s) at risk (OAR). The instructions further comprise assigning a first phase encoding direction parallel to the plane, assigning a second phase encoding direction parallel to the plane, the second phase encoding direction being perpendicular to the first, and assigning a read-out direction that is parallel to the radiation beam. Additionally, the instructions comprise imaging the volume of interest, determining a position of the target volume relative to the radiation beam, and controlling a collimator between the LINAC source and the volume of interest to maintain the radiation beam on the target volume and away from any OAR(s) based on the determined position of the target volume.

According to another aspect, a workstation comprises a processor configured to identify a position of a linear accelerator (LINAC) radiation beam source around a target volume, and identify an imaging plane perpendicular to a radiation beam emitted by the LINAC source. The processor is further configured to assign a first phase encoding direction parallel to the imaging plane, assign a second phase encoding direction different from the first phase encoding direction and parallel to the imaging plane, assign a read-out direction that is parallel to the radiation beam, and present an image a volume of interest that comprises the target volume including phase encoding in the first and second directions and reading out in the read-out direction. Additionally, the processor is configured to determine a position of the target volume relative to the radiation beam, and control the LINAC source to maintain the radiation beam on the target volume and away from any OAR(s) based on the determined position of the volume of interest.

According to another aspect, a method of monitoring a position of a target volume that is being irradiated comprises identifying a position of a linear accelerator (LINAC) radiation beam source around a target volume, identifying an imaging volume of interest defined at one face by a plane perpendicular to a radiation beam emitted by the LINAC source, the volume of interest comprising the target volume and any organ(s) at risk (OAR), assigning a first phase encoding direction parallel to the imaging plane, and assigning a second phase encoding direction parallel the imaging plane, the second phase encoding direction being perpendicular to the first. The method further comprises assigning a read-out direction that is parallel to the radiation beam, imaging the volume of interest, determining a position of the target volume relative to the radiation beam, and controlling a collimator between the LINAC source and the volume of interest to maintain the radiation beam on the target volume and away from any OAR(s) based on the determined position of the volume of interest.

Still further advantages of the subject innovation will be appreciated by those of ordinary skill in the art upon reading and understanding the following detailed description.

The innovation may take form in various components and arrangements of components, and in various steps and arrangements of steps. The drawings are only for purposes of illustrating various aspects and are not to be construed as limiting the invention.

FIG. 4 is an illustration of a combined MR-LINAC imaging and therapy device, such as may be employed in conjunction with the systems and methods described herein.

The subject innovation overcomes the aforementioned problems by addressing a clinical need for improved patient motion monitoring during radiation therapy, using magnetic resonance imaging. Motion in a plane transverse to a linear accelerator (LINAC) beam is monitored to identify target motion. In order to minimize distortion in the transverse plane, phase encoding is performed in two orthogonal directions within the plane, and frequency encoding is performed in the read-out direction (e.g., the direction of the LINAC beam. The relative orientations of the two phase-encode directions can be selected in accordance with the a desired monitoring direction.

Figure 1:
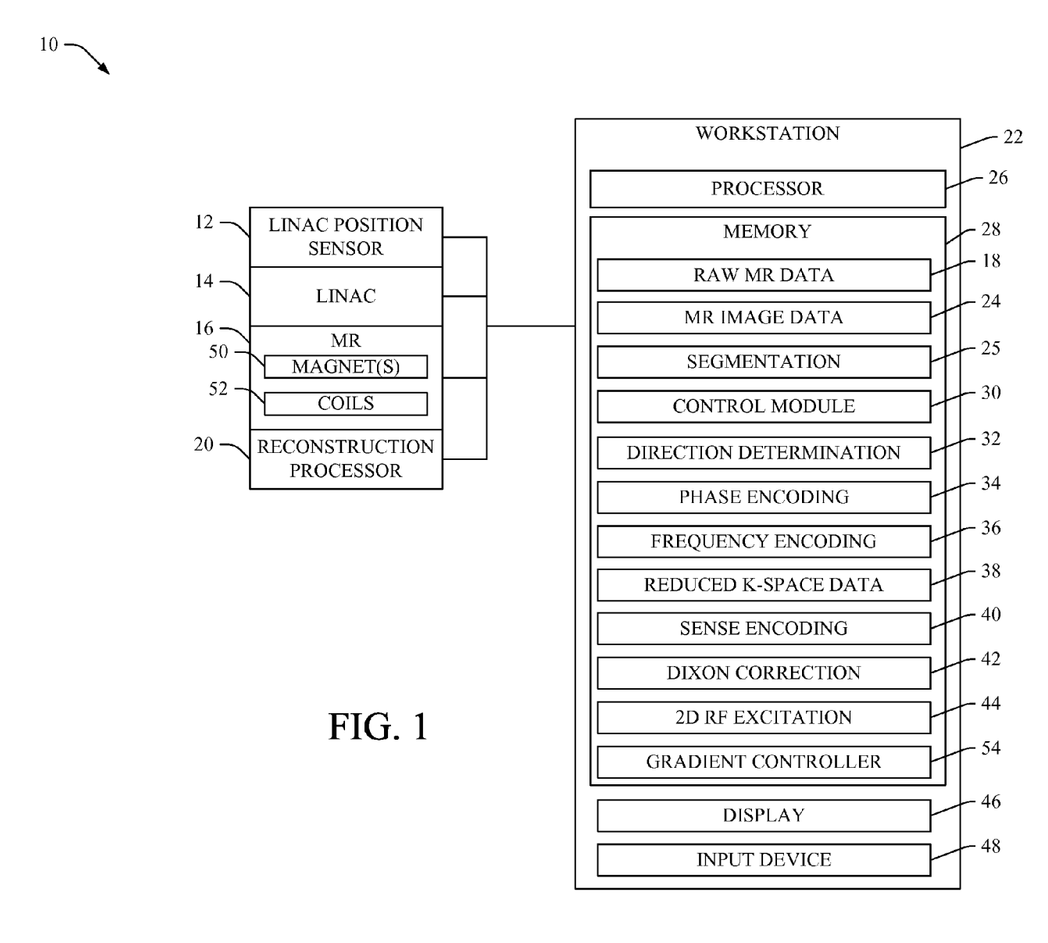
FIG. 1 illustrates a system that facilitates phase encoding in directions linked to an output of a LINAC position sensor, such that the phase encoding is performed in the plane perpendicular to the beam direction.

FIG. 1 illustrates a system 10 that facilitates phase encoding in directions linked to an output of a LINAC position sensor 12, such that the phase encoding is performed in the plane perpendicular to the beam direction. To this end, the system includes the LINAC position sensor 12, which monitors and/or senses a position of a LINAC radiation beam emitted by a LINAC device 14 during a radiation treatment session. The LINAC device is coupled to and/or integrated with a magnetic resonance (MR) scanner 16 that acquires raw data 18 that is reconstructed by a reconstruction processor 20, which may be integral to the MR scanner a workstation 22 or may be separate therefrom, into image data 24 (e.g., a patient image). For instance, the MR scanner transmits raw MR data to the reconstruction processor, which reconstructs the raw data into am MR image, which is stored in the memory. A segmentation module 25 automatically segments the MR images to provide information that is used to keep the radiation beam on the target volume and away from an organ at risk or other volume of interest.

The workstation includes a processor 26 that executes, and a memory 28 that stores, various functions, modules, instructions, routines, etc., for performing the methods, techniques, protocols, and the like described herein. For instance, the memory stores the acquired MR data and the reconstructed MR image data. Additionally, the memory stores a control module 30 that controls the LINAC beam position and rotation as well as the MR device. MRA direction determination module 32 receives LINAC beam position information from the LINAC position sensor 12 and identifies or assigns two phase encoding directions that lie within a plane perpendicular to the LINAC beam. The direction determination module also identifies or assigns a read-out direction that is parallel to the LINAC beam direction. A phase encoding module 34 encodes the phase encoding directions in the imaging plane (i.e., the identified plane, which is perpendicular to the LINAC beam), and a frequency encoding module 36 frequency encodes the read-out direction. Alternatively, the LINAC position can be set and/or detected by a controller independent of the MR system, this LINAC controller communicating with the MR system by means of a digital interface to make the LINAC position available to set the MR slice orientation and encoding directions. As will be appreciated by those of skill in the art, LINAC position control, detection, etc., can be performed by a LINAC controller, an MR controller, a master controller that controls both the LINAC and the MR scanner, a combination of the foregoing, or any other suitable controller for performing the various methods, functions, protocols, etc., described herein. In one embodiment, control of the described system is distributed across one or more of a LINAC controller, MR controller, master controller, etc.

When the 3D imaging technique is performed with both phase-encoding directions in the plane perpendicular to the radiation beam direction, main field inhomogeneity, including the patient susceptibility effects, does not cause spatial distortion of the image information within the plane. Any distortion caused by the gradient non-linearity can be accurately corrected. Automatically linking the imaging directions to the known position of the LINAC gantry 14 ensures the proper phase encoding directions are identified. In order to increase the frame rate, the number of phase-encoding steps is minimized. Using a conventional Cartesian sampling scheme each point in k-space is sampled by executing one MR profile with an appropriate combination of preparation gradients in the two phase-encoding directions. k-space refers to the 2D or 3D Fourier transform of the MR image. Data around the middle of k-space (i.e., central k-space data) predominantly contain contrast information for the image, while data at the periphery of the image contain the information on boundaries in the image. By omitting some of the central and/or peripheral k-space data points 38 that are generated, frame rate is increased but image quality may be degraded.

The present application recognizes that the image need not be either pleasing to the human eye or suitable for diagnosing a disease condition, but instead it should enable tracking of moving organs. One image quality priority, therefore, is that the image is segmentable by an automatic segmentation program. Because the peripheral regions of k-space contribute most strongly to edges and contours in the images, the number of central k-space samples (which contribute to contrast information in the images) can be reduced, in some cases to zero. Additionally fewer than all of the peripheral k-space profiles can be used to provide a minimum level of contour or edge definition to permit the automatic segmentation program to segment the images. The generated k-space samples are stored or buffered in the memory 28. In one embodiment, the image volume is limited such as by using 2D radio frequency (RF) excitation, such that the information from non-relevant regions in the slice need not be phase-encoded. 2D RF excitation can be done more effectively using two or more RF transmit chains (each transmit chain comprising a transmit coil, an RF power amplifier and a waveform generator, controlled by the MR system), (e.g., Transmit-SENSE), which is performed by SENSE module 40. Acquired data points can be further reduced by additionally using receive SENSE encoding. In another embodiment, multi-slice imaging can be performed with correction for distortion in the slice images in the read-out direction. This can be done using a Dixon correction technique such as is performed by a Dixon correction module 42. In this embodiment, the phase encode direction is along the direction in which the measurement of target motion is most critical.

The number of phase encoding steps can be reduced by employing a 2D radio frequency RF excitation module 44 (e.g., zoom imaging). Such excitation can be performed more efficiently if the RF transmit system is n channel Multix-capable (e.g., where n≥2). Limited backfolding and/or ghosting is acceptable as long as the organ to be tracked can be uniquely distinguished from the unwanted information. A learning phase ahead of the actual treatment sequence can be used to automatically select the proper phase encoding directions, field of view, and k-space filling needed to delineate the organ to be tracked. The imaging parameters obtained during this learning phase can be stored in the patient database, to be re-used during subsequent treatment sessions. The learning phase determines how few MR profiles can be generated without compromising the segmentation module's ability to reliably segment the target and any OARs. The image information obtained in the direction parallel to the radiation beam can be used to assess the radiation absorption along the beam, which enables an accurate determination of the radiation dose seen by the tumor and by other tissues.

As stated above, the system 10 includes the processor 26 that executes, and the memory 28 that stores, computer-executable instructions (e.g., routines, programs, algorithms, software code, etc.) for performing the various functions, methods, procedures, etc., described herein. Additionally, "module," as used herein, denotes a set of computer-executable instructions, software code, program, routine, or other computer-executable means for performing the described function, or the like, as will be understood by those of skill in the art.

The memory may be a computer-readable medium on which a control program is stored, such as a disk, hard drive, or the like. Common forms of non-transitory computer-readable media include, for example, floppy disks, flexible disks, hard disks, magnetic tape, or any other magnetic storage medium, CD-ROM, DVD, or any other optical medium, RAM, ROM, PROM, EPROM, FLASH-EPROM, variants thereof, other memory chip or cartridge, or any other tangible medium from which the processor can read and execute. In this context, the systems described herein may be implemented on or as one or more general purpose computers, special purpose computer(s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, Graphical card CPU (GPU), or PAL, or the like.

It will further be understood that the workstation, the MR scanner, and the LINAC device each includes a transceiver for communicating bi-directionally with each other and for communicating with other components of the system. For instance, the workstation receives raw MR data from the MR scanner, reconstructed image data from the reconstruction processor (if not integral to the workstation), LINAC position information from the LINAC position sensor, etc., and transmits control signals to the MR scanner, the LINAC device, and the like. The workstation also includes a display 46 for presenting information (e.g., MR images and/or any other information related to the herein described systems and methods) and an input device 48 (e.g., one or more of a keyboard, mouse, stylus, microphone, touchpad, touchscreen, etc.) via which a user inputs information and/or commands into the workstation.

It will also be understood that the MR scanner includes a main magnet assembly 50 defining a bore into which a subject is placed for imaging during radiation therapy. The main magnet assembly produces a substantially constant main magnetic field oriented along a longitudinal axis of the bore. Although a cylindrical main magnet assembly may be employed, it is to be understood that other magnet arrangements, such as vertical field, open magnets, non-superconducting magnets, and other configurations are also contemplated. A gradient coil 52 produces magnetic field gradients in the bore for encoding magnetic resonance signals, for producing magnetization-spoiling field gradients, or the like. A gradient controller 54, which is depicted as being stored in the memory 28 but which may also reside in the MR scanner itself, controls the gradients generated by the coils during MR data acquisition.

Figure 2:
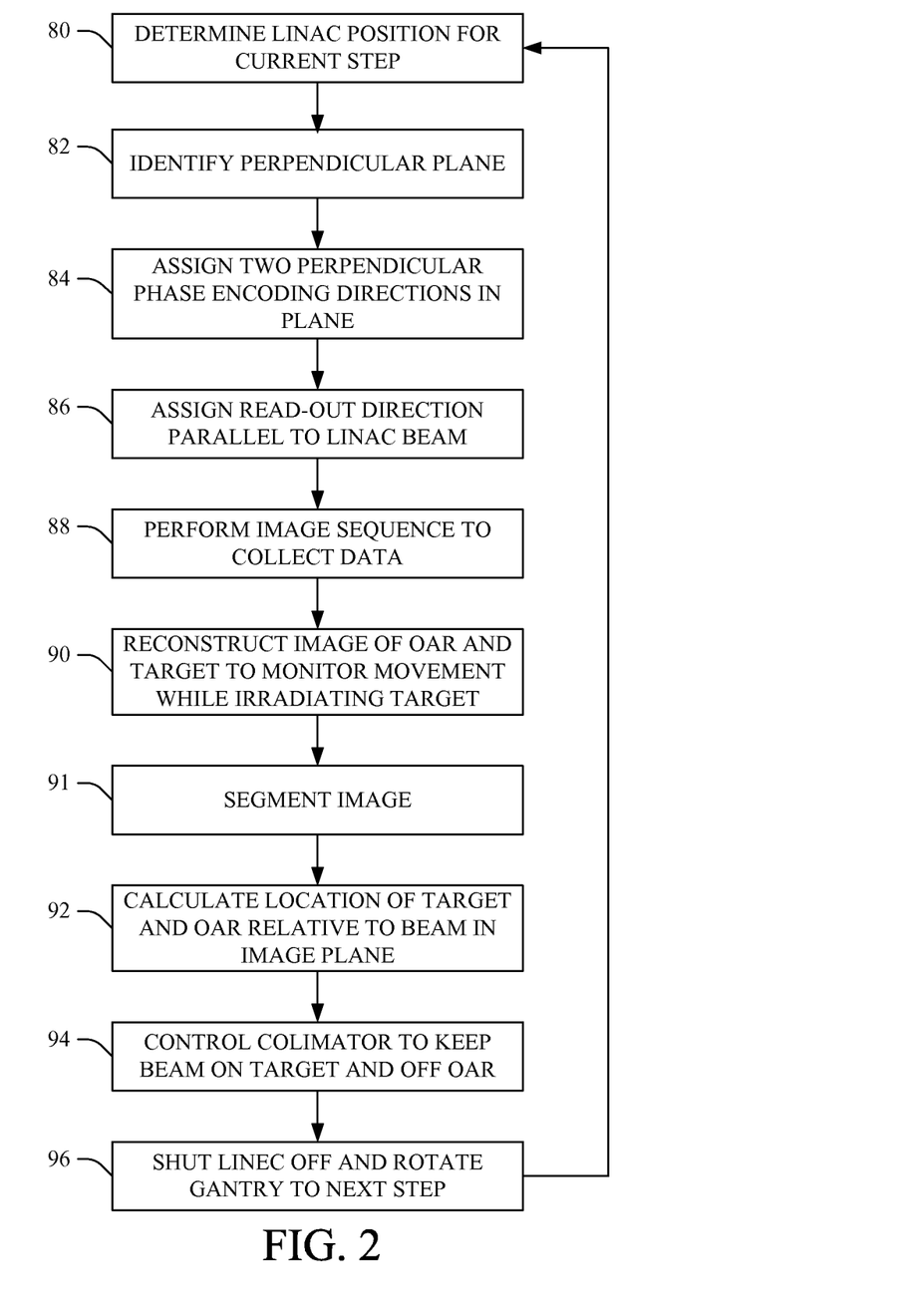
FIG. 2 illustrates a method of tracking motion of an organ at risk (OAR) and/or a volume of interest such as a lesion or tumor being targeted with a radiation beam, such as a LINAC beam or the like, in order to protect the OAR while keeping the beam focused on target.

FIG. 2 illustrates a method of tracking motion of an organ at risk (OAR) and/or a volume of interest such as a lesion or tumor being targeted with a radiation beam, such as a LINAC beam or the like, in order to protect the OAR while keeping the beam focused on target. At 80, LINAC beam position and/or angle is determined for a current radiation step. For instance, the LINAC source and/or beam position can be monitored by a LINAC position sensor. At 82, a plane in the volume of interest and perpendicular to the LINAC beam is identified. More particularly, a volume containing the target with opposite faces parallel to the identified plane is determined. At 84, two phase encoding directions within the identified plane are assigned. The two phase encoding directions are perpendicular to each other. At 86, a read-out direction is assigned, which is parallel to the LINAC beam and therefore perpendicular to the two phase encoding directions.

Once the phase encoding and read-out directions have been assigned, imaging sequences are repeatedly performed, e.g., using a magnetic resonance imager or the like, at 88. At 90, images of the volume containing any OARs and the target volume are repeatedly reconstructed from the acquired scan data. At 91, the target and each OAR are segmented to define their respective boundaries. At 92, a location or position of the target and the OAR and/or a boundary thereof relative to the target volume is determined from the segmented reconstructed image data. Such determination may be made automatically by a processor or the like, or semi-automatically to monitor for patient motion or other events that cause the LINAC beam to be aimed other than on the target. At 94, a collimator on the LINAC source is controlled to adjust beam direction to maintain the LINAC beam on the target volume in real time during therapy delivery and to avoid the OAR(s). At 96, the LINAC radiation beam is shut off, and the LINAC gantry is rotated to a subsequent step. The method reverts to 80 and is iterated until all steps of the radiation treatment have been completed.

Figure 3:
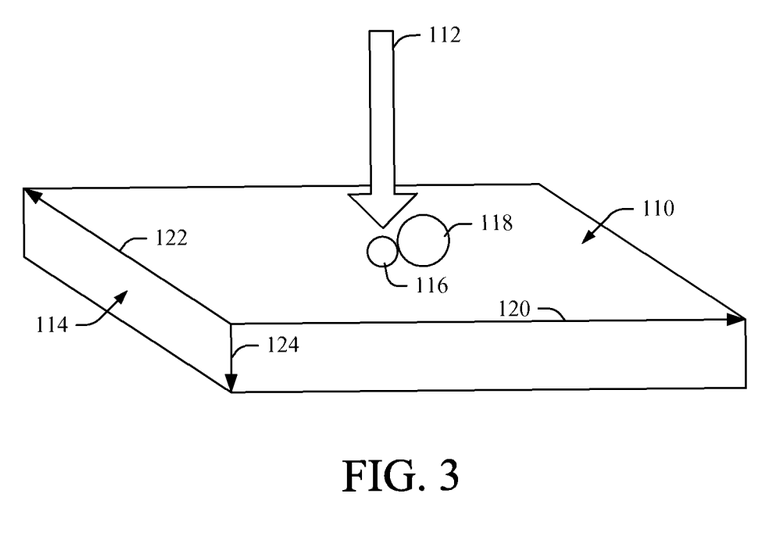
FIG. 3 illustrates an imaging plane that is perpendicular to a LINAC radiation beam.

FIG. 3 illustrates an imaging plane 110 that is perpendicular to a LINAC radiation beam 112 that defines an upper surface of an image volume 114 that contains the target 116 and one or more OAR(s) 118. The phase encoding directions 120, 122 are defined perpendicular to each other and to the LINAC radiation beam. A readout direction 124 is also illustrated as being parallel to the LINAC beam and perpendicular to the phase encoding directions.

FIG. 4 is an illustration of a combined MR-LINAC imaging and therapy device 130, such as may be employed in conjunction with the systems and methods described herein. The combined device 130 includes the LINAC radiation therapy system 14, which rotates about the MR scanner 16 and focuses the radiation beam 112 into an examination region 132 to precisely irradiate the target 116 in a volume of interest 134.

Figure 5A:
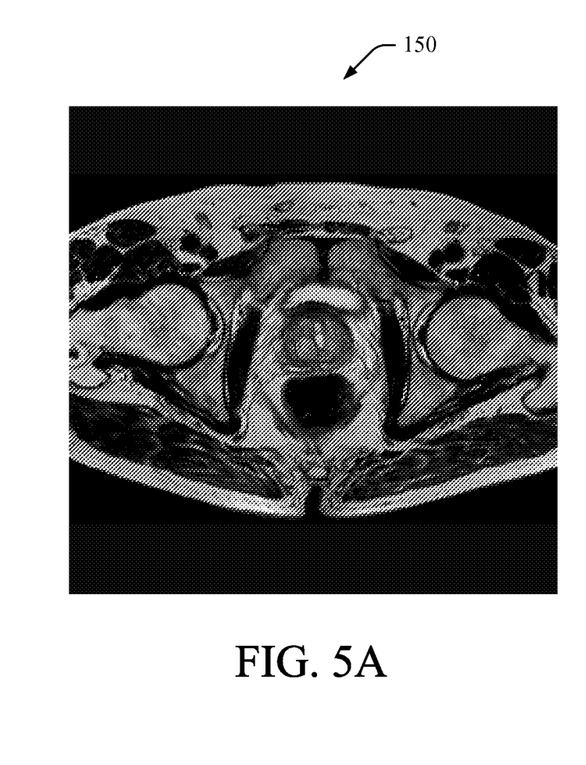
FIGS. 5A and 5B respectively illustrate an MR image generated using a full set of k-space data, and a reduced MR image generated using a reduced set of k-space data.
Figure 5B:
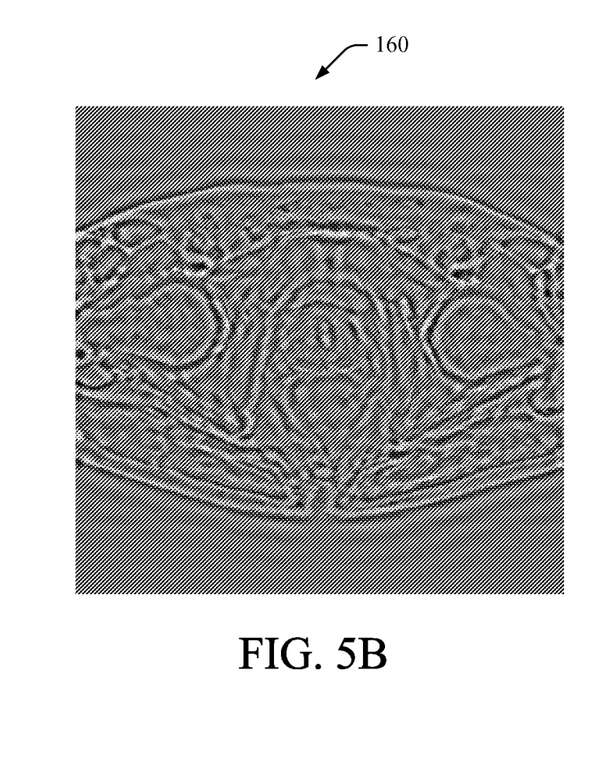

FIGS. 5A and 5B respectively illustrate an MR image 150 generated using a full set of k-space data, and a reduced MR image 160 generated using a reduced set of k-space data. Note that the reduced MR image 160 does not have the photographic quality of the MR image 150, but that the edges of the organs are still identifiable for segmentation. To increase imaging speed, only a fraction of k-space is filled with data when reconstructing the MR image 160. When employing volumetric imaging, the points of k-space are read out individually and not in lines, which permits adjustment of sampling density. Some or all of the data points from a central region of k-space can be eliminated, while many or all of the data points in the boundary areas of k-space are collected. The data points from the boundary areas of k-space contribute most strongly to the edges. Because the MR image is being used to monitor movement of the target organ, the images distinguish the contour of the target and do not need to be high resolution.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

Having thus described the preferred embodiments, the invention is now claimed to be:

1. A system that facilitates monitoring a position of a target volume that is being irradiated, including:
an MR scanner;
a LINAC device; and
a processor configured to execute computer-executable instructions stored in a memory, the instructions comprising:
identifying a position of a linear accelerator (LINAC) radiation beam source around the target volume;
identifying an imaging volume of interest defined at one face by a plane perpendicular to a radiation beam emitted by the LINAC source, the imaging volume of interest comprising the target volume and at least one organ at risk (OAR);
assigning a first phase encoding direction parallel to the plane;
assigning a second phase encoding direction parallel to the plane, the second phase encoding direction being perpendicular to the first phase encoding direction;
assigning a read-out direction that is parallel to the radiation beam;
imaging the imaging volume of interest and the target volume, including phase encoding in the first and second directions and frequency encoding in the read out direction, and collecting fewer central region k-space data points in a central region of k-space than peripheral k-space data points when imaging the imaging volume of interest;
determining a position of the target volume relative to the radiation beam; and
controlling a collimator between the LINAC source and the imaging volume of interest to maintain the radiation beam on the target volume and away from the OAR based on the determined position of the target volume.

2. The system according to claim 1, the instructions further comprising:
collecting fewer than all central k-space data points when imaging the volume of interest.

3. The system according to claim 1, the instructions further comprising:
segmenting the target volume and the OAR to identify boundaries thereof.

4. The system according to claim 1, the instructions further comprising:
performing 2D radio frequency RF excitation to reduce a number of phase encoding steps.

5. The system according to claim 1, the instructions further comprising:
generating at least one test image and determining a minimum acceptable amount of k-space data that can be used to permit monitoring of a boundary of the target volume and the OAR of a subject, and storing one or more parameters defining an imaging sequence used to generate the test image for future use on the subject.

6. A workstation comprising a processor configured to:
identify a position of a linear accelerator (LINAC) radiation beam source around a target volume;
identify an imaging plane perpendicular to a radiation beam emitted by the LINAC source;
assign a first phase encoding direction parallel to the imaging plane;
assign a second phase encoding direction different than the first phase encoding direction and parallel to the imaging plane;
assign a read-out direction that is parallel to the radiation beam;
image a volume of interest that comprises the target volume, including phase encoding in the first and second directions and reading out in the read-out direction, and collecting fewer central region k-space data points in a central region of k-space than peripheral k-space data points when imaging the imaging volume of interest;
determine a position of the target volume relative to the radiation beam; and
control the LINAC source to maintain the radiation beam on the target volume and away from at least one organ (OAR) based on the determined position of the target volume.

7. The workstation according to claim 6, wherein the processor is further configured to:
collect fewer than all central k-space data points when imaging the volume of interest and the target volume.

8. The workstation according to claim 6, wherein the processor is further configured to:
segment the image;
determine a segment boundary of the target volume relative to the radiation beam, and
control the radiation beam to remain on the target volume.

9. The workstation according to claim 6, wherein the processor is further configured to:
perform 2D radio frequency RF excitation to reduce a number of phase encoding steps.

10. The workstation according to claim 6, wherein the processor is further configured to:
generate at least one test image and determining a minimum acceptable amount of k-space data to generate an image that permits reliable segmentation of a boundary of the target volume and the OAR of a subject and store one or more parameters defining an imaging sequence used to generate the test image for future use on the subject.

11. The workstation according to claim 10, wherein the imaging is performed using a magnetic resonance (MR) imaging device.

12. A method of monitoring a position of a target volume that is being irradiated, comprising:
identifying a position of a linear accelerator (LINAC) radiation beam source around a target volume;
identifying a volume of interest defined at one face by a plane perpendicular to a radiation beam emitted by the LINAC source, the volume of interest comprising the target volume and at least one organ at risk (OAR);
assigning a first phase encoding direction parallel to the plane;
assigning a second phase encoding direction parallel to the plane, the second phase encoding direction being perpendicular to the first;
assigning a read-out direction that is parallel to the radiation beam;
imaging the volume of interest, wherein imaging includes collecting fewer central region k-space data points in a central region of k-space than peripheral k-space data points when imaging the imaging volume of interest;
determining a position of the target volume relative to the radiation beam;
controlling a collimator between the LINAC source and the volume of interest to maintain the radiation beam on the target volume and away from the OAR based on the determined position of the target volume.

13. The method according to claim 12, further comprising:
    segmenting the image;
    determining a segment boundary of the target volume relative to the radiation beam; and
    controlling the radiation beam to remain on the target volume.

14. The method according to claim 12, further comprising:
    performing 2D radio frequency RF excitation to reduce a number of phase encoding steps.

15. The method according to claim 12, further comprising:
    generating at least one test image and determining a minimum acceptable amount of k-space data that can be used to permit monitoring of a boundary of the volume of interest of a subject, and storing one or more parameters defining an imaging sequence used to generate the test image for future use on the subject.

16. The method according to claim 12, wherein the imaging is performed using a magnetic resonance (MR) imaging device.

17. A processor or a non-transitory computer-readable medium carrying a computer program that controls one or more processors to perform the method of claim 12.

* * * * *